United States Patent [19]

Baichwal et al.

[11] Patent Number: 5,399,362

[45] Date of Patent: Mar. 21, 1995

[54] ONCE-A-DAY METOPROLOL ORAL DOSAGE FORM

[75] Inventors: Anand Baichwal, Wappingers Falls, N.Y.; Troy W. McCall, New Milford, Conn.

[73] Assignee: Edward Mendell Co., Inc., Patterson, N.Y.

[21] Appl. No.: 232,719

[22] Filed: Apr. 25, 1994

[51] Int. Cl.6 .................................................. A61K 9/22
[52] U.S. Cl. ....................................... 424/488; 424/464; 424/468; 424/469; 424/484; 424/485
[58] Field of Search ............... 424/464, 468, 469, 484, 424/485, 488; 514/651

[56] References Cited

U.S. PATENT DOCUMENTS

| | | | |
|---|---|---|---|
| 4,303,691 | 12/1981 | Sand et al. | 426/573 |
| 4,792,452 | 12/1988 | Howard et al. | 424/475 |
| 4,795,642 | 1/1989 | Cohen et al. | 424/455 |
| 4,824,675 | 4/1989 | Wong et al. | 424/468 |
| 4,857,331 | 8/1989 | Shaw et al. | 424/484 |
| 4,886,669 | 12/1989 | Ventouras | 424/469 |
| 4,894,232 | 1/1990 | Reül et al. | 424/485 |
| 4,942,040 | 7/1990 | Ragnarsson et al. | 424/486 |
| 4,968,508 | 11/1990 | Oren et al. | 424/468 |
| 5,032,406 | 7/1991 | Danereau et al. | 424/464 |
| 5,047,244 | 9/1991 | Sandvordecker et al. | 424/435 |
| 5,128,143 | 7/1992 | Baichwal et al. | 424/464 |
| 5,135,757 | 8/1992 | Baichwal et al. | 424/465 |
| 5,169,639 | 12/1992 | Baichwal et al. | 424/468 |
| 5,271,943 | 12/1993 | Bogart et al. | 424/484 |
| 5,330,763 | 7/1994 | Gole et al. | 424/484 |

*Primary Examiner*—Thurman K. Page
*Assistant Examiner*—Amy Hulina
*Attorney, Agent, or Firm*—Steinberg, Raskin & Davidson

[57] ABSTRACT

A sustained release oral solid dosage form of metoprolol pharmaceutical formulation includes a sustained release excipient including a gelling agent, an inert pharmaceutical diluent, a cationic cross-linking agent. The formulation provides release of metoprolol for at least about 24 hours.

20 Claims, No Drawings

ONCE-A-DAY METOPROLOL ORAL DOSAGE FORM

BACKGROUND OF THE INVENTION

The advantages of controlled release products are well known in the pharmaceutical field and include the ability to maintain a desired blood level of a medicament over a comparatively longer period of time while increasing patient compliance by reducing the number of administrations necessary to achieve the same. These advantages have been attained by a wide variety of methods.

For example, different hydrogels have been described for use in controlled release medicines, some of which are synthetic, but most of which are semi-synthetic or of natural origin. A few contain both synthetic and non-synthetic material. However, some of the systems require special process and production equipment, and in addition some of these systems are susceptible to variable drug release.

Oral controlled release delivery systems should ideally be adaptable so that release rates and profiles can be matched to physiological and chronotherapeutic requirements.

While many controlled and sustained-release formulations are already known, it is often not possible to readily predict whether a particular sustained-release formulation will provide the desired sustained release for a particular drug, and it has generally been found that it is necessary to carry out considerable experimentation to obtain sustained release formulations of such drugs having the desired rate of release when ingested.

There have been a number of patents in the prior art which relate to controlled release metoprolol formulations. For example, U.S. Pat. No. 5,169,638 describes a buoyant controlled release pharmaceutical formulation in the form of a powder filled capsule in which an active ingredient of a basic character exhibits a pH-independent controlled release. The powder comprises the active agent, which may be metoprolol, a water-soluble salt of polyuronic acid, a pH-independent hydrocolloid gelling agent (e.g., hydroxypropylmethylcellulose, methylcellulose or hydroxypropylcellulose), and a binder (HPMC). The formulation is free of calcium ion and carbon dioxide producing material and is said to float gastric juices so that it will have extended residence time in the stomach.

U.S. Pat. No. 4,792,452 describes controlled release pharmaceutical compositions which are said to provide pH-independent release for a basic drug such as metoprolol. The formulations include a pH-dependent polymer which is a salt of alginic acid, a pH-independent hydrocolloid gelling agent and a binder. The salt of the alginic acid is preferably sodium alginate or potassium alginate. The weight ratio of the alginic acid salt to the hydrocolloid gelling agent is all within the range 0.1:1 to 10:1, and the formulation is free of calcium ion and carbon dioxide-producing material.

U.S. Pat. No. 4,957,745 also describes a controlled release metoprolol. The preparation includes a plurality of beads comprising metoprolol coated with a polymeric membrane comprising ethylcellulose with or without hydroxypropylmethylcellulose.

U.S. Pat. No. 4,871,549 describes a time controlled explosion system comprising metoprolol, a swelling agent such as a low substituted hydroxypropylcellulose, sodium starch glycolate or carboxymethylcellulose sodium, coated with a water-insoluble coating material so that drug release is caused by the explosion of the membrane after a definite time period.

U.S. Pat. No. 5,081,154 is directed to metoprolol succinate in an oral composition coated with an anionic polymer soluble at pH over 5.5 and a water insoluble quaternary ammonium substituted acrylic polymer.

Previously, a heterodisperse polysaccharide excipient system and controlled release oral solid dosage forms were described in our U.S. Pat. Nos. 4,994,276, 5,128,143, and 5,135,757, all of which are hereby incorporated by reference. These systems are commercially available under the tradename TIMERx ™ from Edward Mendell Co., Inc., N.Y., which is the assignee of the present invention. These patents are hereby incorporated by reference.

OBJECTS AND SUMMARY OF THE INVENTION

It is an object of the present invention to provide oral solid sustained release formulations which release metoprolol over a time period of at least about 24 hours, when the formulations are exposed to an environment of use (e.g., the gastrointestinal tract).

It is a further object of the present invention to provide methods for preparing sustained release metoprolol formulations which may be administered to patients on a once-a-day basis, or a desired longer time interval.

The above-mentioned objects and others are achieved by virtue of the present invention, which relates in part to a controlled release formulation comprising a therapeutically effective amount of metoprolol, and a sustained release matrix comprising a heteropolysaccharide gum; an inert diluent selected from, e.g., a monosaccharide, a disaccharide, a polyhydric alcohol, or mixtures thereof; and an effective amount of a pharmaceutically acceptable water-soluble cationic cross-linking agent to provide a sustained release of the medicament for at least about 24 hours, when the dosage form is exposed to an environmental fluid.

In certain preferred embodiments of the invention, the gum is included in an amount from about 8% to about 35%, by weight of the final product. The drug to gum ratio may be, e.g., from about 1:1 to about 1:5. More preferably, the drug to gum ratio is from about 1:1.5 to about 1:4.

The present invention is also related to a sustained release oral solid dosage form for metoprolol or a salt thereof, comprising metoprolol or a pharmaceutically acceptable salt thereof in an amount necessary to render a therapeutic effect in a human patient; from about 25% to about 35% heteropolysaccharide gum; and an inert pharmaceutical diluent selected from the group consisting of monosaccharide, a disaccharide, a polyhydric alcohol, and mixtures thereof. The ratio of metoprolol to heteropolysaccharide gum is from about 1:1 to about 1:5. The dosage form provides a sustained release of metoprolol for at least about 24 hours when exposed to an environmental fluid.

The formulations of the present invention are prepared as pharmaceutically acceptable oral solid dosage form, such as tablets.

The present invention is also related to a method for providing a sustained release formulation of metoprolol, comprising preparing a sustained release matrix comprising from about 8 to about 35% of a heteropolysaccharide gum and from about 1 to about 20% of a cationic crosslinking agent capable of crosslinking with the heteropolysaccharide gum agent to increase the gel strength when the gum is exposed to an environmental fluid, and an inert pharmaceutical diluent. The sustained release matrix is combined with metoprolol or a pharmaceutically acceptable salt to provide a drug:gum ratio from about 1:1 to about 1:5; and manufactured into a final product. For example, the resultant mixture may be tableted such that each tablet includes a dose of metoprolol sufficient to provide a therapeutic effect for at least about 24 hours.

The present invention is further related to a method of treating a patient comprising orally administering the sustained release metoprolol tablets to a patient, thereby providing therapeutically effective blood levels of the medicament for at least about 24 hours.

By "sustained release" it is meant for purposes of the present invention that the therapeutically active medicament is released from the formulation at a controlled rate such that therapeutically beneficial blood levels (but below toxic levels) of the medicament are maintained over an extended period of time, e.g., providing a 24 hour dosage form.

The term "environmental fluid" is meant for purposes of the present invention to encompass, e.g., an aqueous solution, such as that used for in-vitro dissolution testing, or gastrointestinal fluid.

DETAILED DESCRIPTION

Metoprolol is a beta$_1$-selective (cardioselective) adronoceptor blocking agent. It reduces oxygen demand of the heart, slowing the heart rate and reducing cardiac output at rest and upon exercise; reduces systolic blood pressure, among other things. The drug is available in the United States in as the tartrate salt (Lopressor ®, Geigy Pharmaceuticals), as 50 mg and 100 mg tablets. The effective daily dose is 100 mg to 450 mg, and Lopressor is usually dosed as 100 mg given in two daily doses. Metoprolol is also available as 50 mg, 100 mg and 200 mg extended release tablets in the United States as the succinate salt (Toprol XL TM, Astra Pharmaceutical Products, Inc.), which may be dosed once daily.

As reported in our previously in our U.S. Pat. Nos. 4,994,276, 5,128,143, and 5,135,757, the heterodisperse excipient of the present invention comprising both hetero- and homo-polysaccharides which exhibit synergism, e.g., the combination of two or more polysaccharide gums produce a higher viscosity and faster hydration than that which would be expected by either of the gums alone, the resultant gel being faster-forming and more rigid.

In the present invention, it has been found that a sustained release excipient comprising only the heteropolysaccharide, e.g., xanthan gum, is sufficient to provide a suitable sustained release of an insoluble medicament to provide a 24 hour formulation, nor to prevent an initial "burst" of drug release from the formulation when the formulation is exposed to a fluid in an environment of use, e.g. an aqueous solution or gastrointestinal fluid.

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties.

An especially preferred heteropolysaccharide is xanthan gum, which is a high molecular weight ($>10^6$) heteropolysaccharide. Other preferred heteropolysaccharides include derivatives of xanthan gum, such as deacylated xanthan gum, the carboxymethyl ether, and the propylene glycol ester.

The sustained release formulations of the present invention are substantially insensitive to the solubility of the medicament and likewise insensitive to the pH changes along the length of the gastrointestinal tract. Thus, the formulations of the present invention are pH-independent.

In certain preferred embodiments where the sustained release of the medicament is provided substantially only by the heteropolysaccharide, the sustained release metoprolol formulation comprises from about 25% to about 35% heteropolysaccharide gum.

In other preferred embodiments, the sustained release matrix further includes a cationic cross-linking agent, e.g., monovalent or multivalent metal cations. The preferred salts are the inorganic salts, including various alkali metal and/or alkaline earth metal sulfates, chlorides, borates, bromides, citrates, acetates, lactates, etc. Specific examples of suitable cationic cross-linking agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred cationic cross-linking agents are bivalent. Particularly preferred salts are calcium sulfate and sodium chloride. In such embodiments, the heteropolysaccharide gum is preferably included in an amount from about 8% to about 35% of the formulation, and the cationic cross-linking agent is included in the sustained release excipient of the present invention in an amount from about 1% to about 20% by weight of the sustained release excipient, and in an amount from about 1% to about 20% by weight of the final dosage form. In preferred embodiments of the present invention, the heteropolysaccharide comprises from about 15% to about 30% of the sustained release matrix and cationic cross-linking agent comprises about 10% by weight of the sustained release matrix.

The inert filler of the sustained release matrix preferably comprises a pharmaceutically acceptable saccharide, including a monosaccharide, a disaccharide, or a polyhydric alcohol, and/or mixtures of any of the foregoing. Examples of suitable inert pharmaceutical fillers include sucrose, dextrose, lactose, microcrystalline cellulose, fructose, xylitol, sorbitol, mixtures thereof and the like. However, it is preferred that a soluble pharmaceutical filler such as lactose, dextrose, sucrose, or mixtures thereof be used.

The sustained release matrixes of the invention have uniform packing characteristics over a range of different particle size distributions and are capable of processing into tablets using either direct compression, following addition of drug and lubricant powder or conventional wet granulation. In wet granulation techniques, the desired amounts of the heteropolysaccharide gum, with or without the cationic cross-linking agent, and the inert diluent are mixed together and thereafter a moistening agent such as water, propylene glycol, glycerol, alcohol or the like is added to prepare a moistened mass. Next, the moistened mass is dried. The dried mass is then milled with conventional equipment to obtain the desired particle size.

Once the sustained release excipient of the present invention has been prepared, it is then possible to blend the same with metoprolol, e.g., in a V-blender or via wet granulation. An effective amount of any generally accepted pharmaceutical lubricant, including the calcium or magnesium soaps may be added to the above-mentioned ingredients of the excipient at the time the medicament is added, or in any event prior to compression into a solid dosage form. An example of a suitable lubricant is magnesium stearate in an amount of about 0.5% to about 3% by weight of the solid dosage form. An especially preferred lubricant is sodium stearyl fumarate, NF, commercially available under the trade name Pruv ® from the Edward Mendell Co., Inc.

In certain preferred embodiments of the invention, the sustained release matrix further comprises a hydrophobic material in an amount effective to slow the hydration of the gum without disrupting the hydrophilic matrix formed by the heteropolysaccharide when the formulation is exposed to fluids in an environment of use. This may be accomplished by granulating the sustained release matrix with a solution or dispersion of hydrophobic material prior to the incorporation of the medicament. The hydrophobic material may be selected from ethylcellulose, acrylic and/or methacrylic acid polymers or copolymers, hydrogenated vegetable oils, zein, as well as other pharmaceutically acceptable hydrophobic materials known to those skilled in the art. Other hydrophobic cellulosic materials such as other alkyl celluloses may also be used. The amount of hydrophobic material incorporated into the sustained release matrix is that which is effective to slow the hydration of the gums without disrupting the hydrophilic matrix formed upon exposure to an environmental fluid. In certain preferred embodiments of the present invention, the hydrophobic material may be included in the sustained release matrix in an amount from about 1% to about 20% by weight. More preferably, the hydrophobic material may be included in the sustained release matrix in an amount from about 3% to about 12%, and most preferably from about 5% to about 10%, by weight of the final formulation. The hydrophobic material may be dissolved in an organic solvent or dispersed in an aqueous solution for incorporation into the formulation.

The dosage forms of the present invention are preferably tablets. However, the ingredients may also be formulated in a capsule, extruded and spheronized with an active medicament to form pellets, etc.

In certain embodiments, the complete mixture in an amount sufficient to make a uniform batch of tablets is then subjected to tableting in a conventional production scale tableting machine at normal compression pressure, i.e. about 2000-1600 lbs/sq in. However, the mixture should not be compressed to such a degree that there is subsequent difficulty in achieving hydration when exposed to gastric fluid. The average tablet weight may be from about 300 mg to 950 mg. For metoprolol tablets which are to contain about 100 mg of drug, the tablet weight is preferably from about 450 mg to 950 mg.

The average particle size of the granulated excipient of the present invention ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 6 to about 8 kg hardness. The average flow of the granulations prepared in accordance with the present invention are from about 25 to about 40 g/sec. Tablets compacted using an instrumented rotary tablet machine have been found to possess strength profiles which are largely independent of the inert saccharide component. Scanning electron photomicrographs of largely tablet surfaces have provided qualitative evidence of extensive plastic deformation on compaction, both at the tablet surface and across the fracture surface, and also show evidence of surface pores through which initial solvent ingress and solution egress may occur.

The amount of metoprolol or salt thereof incorporated into the unit dose formulations (e.g., tablets) of the present invention may be 50 mg, 100 mg or 200 mg, based on the tartrate salt. Of course, if other metoprolol salts are to be used, the weight of the particular metoprolol salt to be included may be calculated based on an equivalent weight to the tartrate salt.

DETAILED DESCRIPTION OF THE PREFERRED EMBODIMENTS

The following examples illustrate various aspects of the present invention. They are not to be construed to limit the claims in any manner whatsoever.

EXAMPLES 1-3

The sustained release excipient is prepared by dry blending the requisite amounts of xanthan gum, dextrose and calcium sulfate in a high-speed mixer/granulator for 2 minutes. While running choppers/impellers, the water is added and the mixture is granulated for another 2 minutes. The granulation is then dried in a fluid bed dryer to a loss on drying weight (LOD) of between 4 and 7%. The granulation is then milled using 20 mesh screens. The ingredients of the sustained release excipient of Example 1 are set forth in Table 1 below:

TABLE 1

| PREPARATION OF SUSTAINED RELEASE EXCIPIENT | | | |
|---|---|---|---|
| Component | % - Ex. 1 | % - Ex. 2 | % - Ex. 3 |
| 1. Xanthan gum | 30 | 15 | 30 |
| 2. Dextrose | 60 | 75 | 70 |
| 3. Calcium Sulfate | 10 | 10 | 0 |
| 4. Water | 10* | 10* | 10* |

*removed during processing

Next, the sustained release excipient prepared as detailed above is dry blended with a desired amount of medicament (in the following examples metoprolol, provided as the tartrate salt) in a V-blender for 10 minutes. A suitable amount of tableting lubricant Pruv ® (sodium stearyl fumarate, NF, commercially available from the Edward Mendell Co., Inc.) for the following examples is added and the mixture is blended for another 5 minutes. This final mixture is compressed into tablets, each tablet containing 100 mg metoprolol. The tablets of Example 1 weighed 618.5 mg. The tablets of Example 2 weighed 618.5 mg. The tablets of Example 3 weighed 618.5 mg. The drug:gum ratio of the tablets of Example 1 was 1:1.5. The drug:gum ratio of the tablets of Example 2 was 1:.75. The drug:gum ratio of the tablets of Example 3 was 1:1.5. The ingredients of the tablets of Examples 1-3 are set forth in Table 2 below:

TABLE 2

| Component | % |
|---|---|
| 1. Sustained Release Excipient | 80.8% |
| 2. Metoprolol | 16.2% |
| 3. Pruv ® | 3.0% |

Dissolution tests were then carried out on the tablets of Examples 1-3. The dissolution tests are conducted in an automated USP dissolution apparatus (Paddle Type II, pH 6.8 buffer, 100 rpm.) The results are set forth in Table 3 below:

TABLE 3

| | Effect of Single Gum Composition | | |
|---|---|---|---|
| Time(hours) | Example 1 | Example 2 | Example 3 |
| 0 | 0.0 | 0.0 | 0.0 |
| 2 | 25.3 | 29.0 | 20.7 |
| 4 | 37.9 | 42.7 | 32.3 |
| 8 | 56.3 | 63.6 | 50.2 |
| 12 | 70.6 | 77.9 | 64.1 |
| 16 | 81.3 | 88.2 | 74.3 |
| 20 | 89.0 | 94.9 | 81.3 |
| 24 | 97.6 | 98.8 | — |

From the results provided in Table 3, it can be seen that formulations made with a greater concentration of gum produced slower drug release rates. It is also evident that the incorporation of calcium sulfate into single gum systems results in a faster drug release rates compared to formulations without calcium sulfate. Accordingly, the results provide that the tablets in Example 1 are suitable for delivering medicaments as an oral solid dosage form over a 24-hour oral period of time.

The examples provided above are not meant to be exclusive. Many other variations of the present invention would be obvious to those skilled in the art, and are contemplated to be within the scope of the appended claims.

What is claimed is:

1. A tablet for the sustained release of metoprolol or a salt thereof, comprising:
   metoprolol or a pharmaceutically acceptable salt thereof in an amount necessary to render a therapeutic effect in a human patient;
   from about 8% to about 35% heteropolysaccharide gum;
   from about 0.5% to about 20% of a cationic cross-linking agent selected from the group consisting of alkali metal and alkaline earth metal sulfates, chlorides, borates, bromides, citrates, acetates, lactates and mixtures thereof and capable of crosslinking with said heteropolysaccharide gum to increase the gel strength when said formulation is exposed to an environmental fluid;
   an inert pharmaceutical diluent selected from the group consisting of monosaccharide, a disaccharide, a polyhydric alcohol, and mixtures thereof;
   the ratio of metoprolol to said heteropolysaccharide gum being from about 1:1 to about 1:5, said dosage form providing a sustained release of metoprolol for at least about 24 hours when exposed to an environmental fluid.

2. The oral solid dosage form of claim 1, wherein the drug to gum ratio is from about 1:1.5 to about 1:4.

3. The oral solid dosage form of claim 1, wherein said cationic cross-linking agent comprises calcium sulfate.

4. The oral solid dosage form of claim 1, wherein said cationic cross-linking agent comprises about 10 percent of said formulation, by weight.

5. The oral solid dosage form of claim 1, further comprising a hydrophobic polymer selected from the group consisting of an alkylcellulose, an copolymer of acrylic and methacrylic esters, and mixtures thereof prior to incorporation of said medicament, said hydrophobic polymer being included in said dosage form in an amount effective to slow the hydration of said gums when exposed to an environmental fluid.

6. The oral solid dosage form of claim 5, wherein said hydrophobic polymer comprises ethylcellulose.

7. The oral solid dosage form of claim 5, wherein said hydrophobic material comprises from about 1 to 20 percent of said dosage form, by weight.

8. The oral solid dosage form of claim 5, wherein said hydrophobic polymer comprises from about 5 to about 10 percent of said dosage form, by weight.

9. The oral solid dosage form of claim 1, which comprises 50 mg, 100 mg, or 200 mg of metoprolol.

10. A method of preparing a 24 hour formulation of metoprolol, comprising:
   preparing a sustained release matrix comprising from about 8 to about 35% of a heteropolysaccharide gum and from about 1 to about 20% of a cationic crosslinking agent selected from the group consisting of alkali metal and alkaline earth metal sulfates, chlorides, borates, bromides, citrates, acetate, lactates and mixtures thereof and capable of crosslinking with said heteropolysaccharide gum agent to increase the gel strength when said gum is exposed to an environmental fluid, and an inert pharmaceutical diluent;
   combining said sustained release matrix with metoprolol or a pharmaceutically acceptable salt to provide a drug:gum ratio from about 1:1 to about 1:5; and
   tableting the resultant mixture such that each tablet includes a dose of metoprolol sufficient to provide a therapeutic effect for at least about 24 hours.

11. The method of claim 10, further comprising adding a hydrophobic material to said mixture of said sustained release matrix and said metoprolol prior to tableting in an amount effective to slow the hydration of said gum when exposed to an environmental fluid.

12. The method of claim 10, further comprising providing said tableted formulation with a drug to gum ratio from about 1:1.5 to about 1:4.

13. The method of claim 10, wherein said hydrophobic polymer is selected from the group consisting of an alkylcellulose, an copolymer of acrylic and methacrylic esters, and mixtures thereof.

14. The method of claim 11, wherein said hydrophobic polymer comprises ethylcellulose and said cationic cross-linking agent comprises calcium sulfate.

15. The method of claim 14, wherein said hydrophobic material comprises from about 1 to 10 percent of said dosage form, by weight.

16. The method of claim 12, further comprising tableting said mixture of such that each tablet contains from about 50 mg to about 200 mg metoprolol or a pharmaceutically acceptable salt thereof.

17. A method of treating a patient with metoprolol, comprising, preparing a sustained release matrix comprising from about 8 to about 35% of a heteropolysaccharide gum and from about 1 to about 20% of a cationic crosslinking agent selected from the group consisting of alkali metal and alkaline earth metal sulfates, chlorides, borates, bromides, citrates, acetates, lactates and mixtures thereof and capable of crosslinking with said heteropolysaccharide gum agent to increase the gel strength when said gum is exposed to an environmental fluid, and an inert pharmaceutical diluent;

combining said sustained release excipient with metoprolol or a pharmaceutically acceptable salt to provide a drug:gum ratio from about 1:1 to about 1:5; and tableting the resultant mixture such that each tablet includes a dose of metoprolol sufficient to provide a therapeutic effect for at least about 24 hours, and administering said tablets to a patient at an appropriate dosing interval.

18. The method of claim 17, further comprising tableting said resultant mixture such that each tablet includes 50 mg, 100 mg, or 200 mg of metoprolol.

19. The oral solid dosage form of claim 1, wherein said heteropolysaccharide gum is present in an amount of from about 25% to about 35%.

20. The tablet of claim 1, wherein said heteropolysaccharide gum is xanthan gum.

* * * * *